(12) United States Patent
Beebe

(10) Patent No.: US 8,511,517 B2
(45) Date of Patent: Aug. 20, 2013

(54) PROTECTIVE SYRINGE SLEEVE

(75) Inventor: W. Scott Beebe, Berkley, MA (US)

(73) Assignee: Fishman Corporation, Hopkinton, MA (US)

( * ) Notice: Subject to any disclaimer, the term of this patent is extended or adjusted under 35 U.S.C. 154(b) by 751 days.

(21) Appl. No.: 12/612,914

(22) Filed: Nov. 5, 2009

(65) Prior Publication Data

US 2011/0101035 A1    May 5, 2011

(51) Int. Cl.
*G01F 11/00* (2006.01)
(52) U.S. Cl.
USPC .......................................... 222/386; 604/246
(58) Field of Classification Search
USPC .............. 222/326, 386, 386.5; 604/199, 246
See application file for complete search history.

(56) References Cited

U.S. PATENT DOCUMENTS

| | | | |
|---|---|---|---|
| 2,847,996 A | 8/1958 | Cohen et al. | |
| 3,965,897 A * | 6/1976 | Lundquist | 604/246 |
| 7,077,826 B1 * | 7/2006 | Gray | 604/171 |
| 7,754,494 B1 * | 7/2010 | Verkaart et al. | 436/180 |
| 2002/0017294 A1 * | 2/2002 | Py | 128/200.23 |

FOREIGN PATENT DOCUMENTS

| WO | WO 99/24098 | 5/1999 |
|---|---|---|
| WO | WO 99/45851 | 9/1999 |

OTHER PUBLICATIONS

International Search Report issued in corresponding PCT Application No. PCT/US2010/002880, mailed Mar. 16, 2011.
International Preliminary Report on Patentability issued in corresponding PCT Application No. PCT/US2010/002880, mailed May 18, 2012.

* cited by examiner

*Primary Examiner* — Kevin P Shaver
*Assistant Examiner* — Melvin Cartagena
(74) *Attorney, Agent, or Firm* — Mirick, O'Connell, DeMallie & Lougee, LLP

(57) ABSTRACT

A protective sleeve placed within the cylinder of a syringe, the sleeve protects a piston and a computer controlled device or human operator pushing the piston from material leaking past a piston assembly. The sleeve has lips or ridges at either end, one that is attached to the piston assembly at the output end of the syringe and a second lip that is attached with a retention plate at the far end of the syringe. The sleeve may have a bellows or accordion configuration that slides along the inner surface of the syringe cylinder without appreciably loading the drive mechanism.

10 Claims, 3 Drawing Sheets

PROTECTIVE SYRINGE SLEEVE

BACKGROUND OF THE INVENTION

1. Field of the Invention

The present application relates to sleeves that protect the operation of syringes.

2. Background Information

Syringes are typically cylindrical in shape and equipped with an internally encased piston or piston assembly that pushes a substance within the cylinder and delivers the substance to an output port that is typically a hollow needle. Hereinafter the phrase "piston assembly" is defined to include a single piston and/or a piston assembly made from component parts. The piston is withdrawn from within the cylinder and the cylinder is filled with a substance. The piston is repositioned within the cylinder and pushed towards the output port ejecting the substance through the hollow needle to some desired location.

In applications where the substance is potentially harmful or detrimental, such as cyanoacrilate adhesives or solder paste, or where precise metering of the substance is desired, it is prudent to prevent the substance from leaking around the piston. The piston typically has a seal meant to prevent substances from passing between the piston and the inner cylinder wall, however in some cases, particularly with very viscous substances, the seal may fail and allow leakage of the substance to an area behind the piston.

In some applications, the piston may be operated by a human and leakage around the piston seal may contact the human with potentially harmful results. In other applications the piston-may be pushed via computer controlled device, e.g. a motor and lead screw. In these other applications, however, preventing leakage remains important since the substance within the cylinder may contact the piston advancing means of the computer controlled device and the resulting contamination may then be returned to the computer controlled device itself, potentially causing the device to fail.

SUMMARY OF THE INVENTION

The present disclosure describes a protective sleeve that is installed within a syringe cylinder. The sleeve is positioned with one end at the piston assembly and the other end at the far end of the cylinder. The sleeve is specially formed with two ends, one end is attached or fixed to on end of the cylinder and the sleeve's second end is attached to and moves with the piston. Any substance in the cylinder that may leak by the piston at the cylinder wall will be prevented protective sleeve from reaching the piston, the drive shaft and the motor or computer electronics driving the piston.

The protective sleeve has a tubular shape that is collapsible along the long axis of the tube and the axis of the cylinder. The sleeve may be made from of a resilient material. Illustrative, one collapsible shape is a bellows that extends and compresses easily, however other shapes may function similarly. The end of the sleeve attached to a piston or piston assembly moves with the piston or piston assembly while the other end remains fixed in place.

The sleeve may have a first lip or ridge that engages the piston assembly, wherein the first lip moves with the piston assembly; and a second lip that is retained at the far end of the syringe. The first lip may engage a recess in the piston or be bonded or otherwise fixed to the piston assembly. The second lip may be retained at the other end of the syringe by a plate or it also may be bonded or fixed to the other end of the syringe. The sleeve extends and collapses as the piston assembly moves in both directions along the long axis of the cylinder.

In one application the sleeve's tubular shape includes a bellows along at least a portion of the sleeve.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
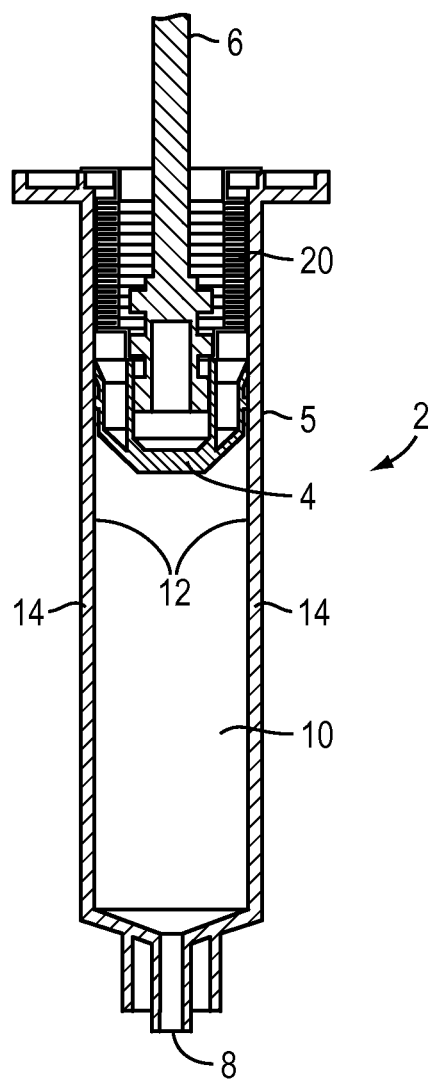
FIG. 1 is a sectioned drawing of a fully compressed protective sleeve installed in a syringe.

FIG. 1 illustrates a syringe 2 with a piston 4 that is attached to and being pushed by a shaft 6 controlled by a computer controlled device. In this example, the shaft 6 is an extendable and retractable leadscrew driven by a motor (not shown). The syringe has an outlet 8 and a protective sleeve 20 that is compressed. In FIG. 1, a substance that is contained in the volume 10 may be delivered via the outlet 8 by the shaft 6 pushing the piston assembly 4 that in turn expels the substance. The piston assembly may include a hub and seal, as would be known to those skilled in the art.

The substance in the volume 10 may leak where the outer edge seal of the piston assembly 10 meets the inner surface 12 of the syringe cylinder 14.

Figure 2B:
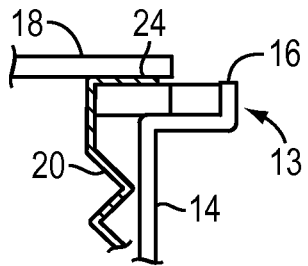
FIGS. 2B and 2C illustrate the lips on either end of the sleeve that lock and seal the sleeve.
Figure 2C:
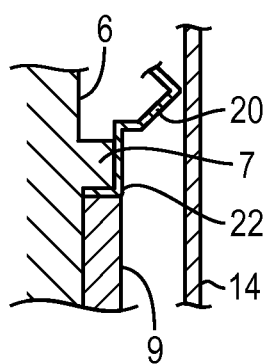
Figure 2A:
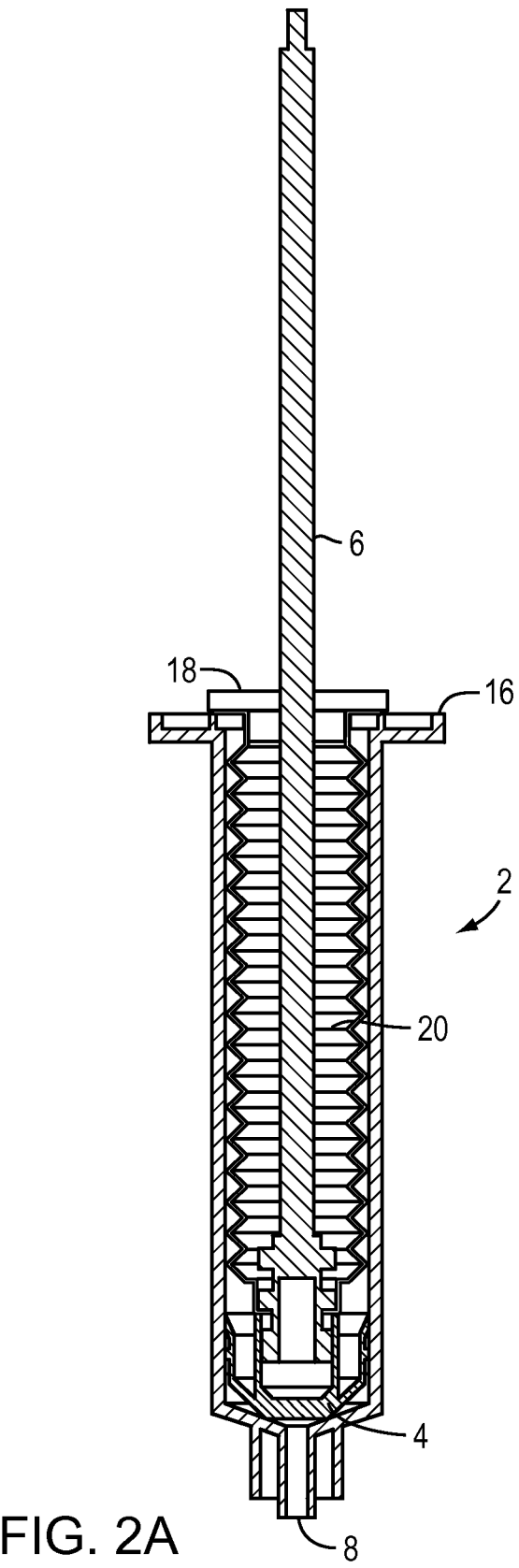
FIG. 2A is a sectioned drawing of a fully extended protective sleeve installed in a syringe.

FIG. 2A shows the piston assembly after expelling most of the contents of the volume 10 and the protective sleeve is fully extended. Comparing FIG. 1 and FIG. 2A, if some of the contents of the volume 10 leaked by the piston and remained on the cylinder wall and if the protective sleeve 20 were not in place, the contents might contact the shaft 6, and, as mentioned above, the contents may be returned to the computer controlled device and cause damage, malfunction, or failure.

FIG. 2B shows a functional detail where a lip 24 of the sleeve 20 is secured between a retention plate 18 at the end 13 of the cylinder 14. FIG. 2C illustrates the sleeve attachment at the outlet of the syringe. Here the lip 22 of the sleeve 20 is secured between an extension 9 of the piston assembly 14 and a shoulder 7 of the shaft 6.

Figure 3:
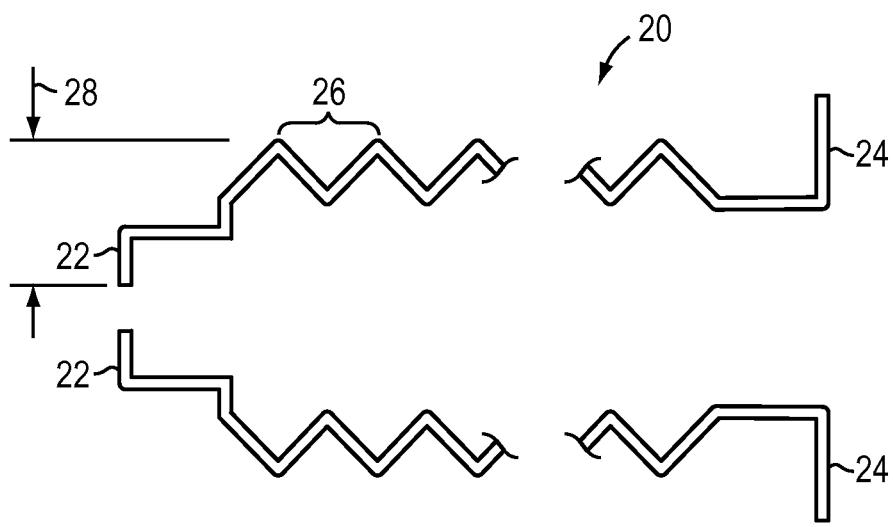
FIG. 3 is a side drawing of a fully extended sleeve.

FIG. 3 is a sectioned view of the sleeve 20 illustrating the lip 24 and the lip 22 at distal ends of the sleeve.

As is evident from all the drawings in this particular example, the sleeve has a tubular shape with a "bellows" or "accordion" configuration 26 to accommodate a full compression when the syringe is full and a full extension when the syringe has emptied its contents. Thinner material is advantageous as it will allow for more volume of material to be loaded within the syringe, due to reduced full compression height of the sleeve. The sleeve will easily extend along the long axis of the tubular shape and the cylinder of the syringe and will move back up the cylinder as the shaft 6 pulls the piston back. A pull back may be used to prevent leaking at the outlet 8 by creating a vacuum that holds the contents within the syringe. The sleeve, with this configuration, is designed to minimally, if at all, increase the dynamic load on the computer controlled device. The depth 28 of the protective sleeve is arranged to allow the shaft entry without interference.

The sleeve may be made from low density resilient polyethylene, or other resilient materials, with a very thin wall, perhaps only 0.015" thick. Other wall thicknesses, however, may be employed depending on the configuration of the syringe into which the protective sleeve is installed. It may be fabricated by a blow molding process, but other processes may be used as known to those in the art. The thickness limits the range of the travel from full compression to full extension, as shown in FIG. 1 and full extension in FIG. 2A.

The bellows shape is illustrative, and other configurations may be used. For example, screw shaped ridges that compress or tube sections of different diameters where on section telescopes into another section may be used.

In some applications the sleeve is installed in pre-filled syringes, and is meant as a single use device that is discarded with the syringe after use. Since syringes are manufactured in different sizes and configuration, the subject protective sleeve may be made in many different sizes, thicknesses and configurations.

What is claimed is:

1. A protective sleeve for use in a syringe having a cylinder with a first and second ends, a piston assembly, an output at the first end and an opening for a shaft at the second end of the cylinder, the protective sleeve comprising:
   a tube having a first end and a second end, the second end opposing the first end, the tube configured to compress and expand along a longitudinal axis of the tube, the sleeve made of a resilient material that is placed within the cylinder behind the piston assembly;
   a first lip formed at one end of the tube shape that is configured to engage the piston assembly and to move with the piston assembly, the first lip having:
      a first lip longitudinal portion extending from the sleeve along a direction substantially parallel to the longitudinal axis of the tube, and
      a first lip radial portion extending from the first lip longitudinal portion along a direction that is substantially perpendicular to the longitudinal axis of the tube; and
   a second lip formed at the second end of the tube shape that is configured to be retained at the second end of the cylinder, wherein the collapsible tubular shape is configured to extend and collapse as the piston assembly moves, the second lip having
      a second lip longitudinal portion extending from the tube along a direction substantially parallel to the longitudinal axis of the tube, and
      a second lip radial portion extending from the second lip longitudinal portion along a direction that is substantially perpendicular to the longitudinal axis of the tube;
   the first lip radial portion configured to be captured between a shoulder of the shaft and an extension portion of the piston assembly; and
   the second lip radial portion configured to be captured between a retaining plate and the second end of the cylinder.

2. The protective sleeve of claim 1 further wherein the tubular shape comprises a bellows or accordion configuration along at least a portion of the sleeve.

3. The protective sleeve of claim 1 wherein the sleeve is made from polyethylene, or other resilient material of a thickness of less than 0.15 inches.

4. The protective sleeve of claim 1, wherein the second lip radial portion is configured to be disposed external to the second end of the cylinder between the retaining plate and a handle of the cylinder.

5. The protective sleeve of claim 1, wherein the second lip radial portion extends radially inward toward a central axis of the tube.

6. The protective sleeve of claim 1, wherein the first lip radial portion extends radially outward from a central axis of the tube.

7. A syringe comprising:
   a cylinder with two ends, a first end defining an output and a second end defining an opening for a shaft;
   a piston assembly; and
   a tubular shaped sleeve made to compress and expend along a longitudinal axis of the tube, the sleeve made of a resilient material that is placed within the cylinder behind the piston assembly;
   the sleeve having a first lip that is fixed to the piston assembly, wherein the end of the protective sleeve with the first lip moves with the piston assembly, the first lip having:
      a first lip longitudinal portion extending from the sleeve along a direction substantially parallel to the longitudinal axis of the tube, and
      a first lip radial portion extending from the first lip longitudinal portion along a direction that is substantially perpendicular to the longitudinal axis of the tube,
      the first lip radial portion captured between a shoulder of the shaft and an extension portion of the piston assembly; and
   the sleeve having a second lip that is retained at the second end of the cylinder, wherein the collapsible tubular shape extends and collapses as the piston assembly moves forward and back within the cylinder, the second lip having
      a second lip longitudinal portion extending from the tube along a direction substantially parallel to the longitudinal axis of the tube, and
      a second lip radial portion extending from the second lip longitudinal portion along a direction that is substantially perpendicular to the longitudinal axis of the tube,
      the second lip radial portion captured between a retaining plate and the second end of the cylinder.

8. The syringe of claim 7, wherein the second lip radial portion is disposed external to the second end of the cylinder between the retaining plate and a handle of the cylinder.

9. The syringe of claim 7, wherein the second lip radial portion extends radially inward toward a central axis of the tube.

10. The syringe of claim 7, wherein the first lip radial portion extends radially outward from a central axis of the tube.

* * * * *